United States Patent [19]

Fouquay

[11] Patent Number: 5,296,633
[45] Date of Patent: Mar. 22, 1994

[54] HMTA PREPARATION OF METHYLATED TERTIARY AMINES

[76] Inventor: Stephane Fouquay, 7, Parc de la Saane, 76130 Mont Saint-Aignan, France

[21] Appl. No.: 998,596

[22] Filed: Dec. 30, 1992

[30] Foreign Application Priority Data

Dec. 30, 1991 [FR] France .................... 91 16316

[51] Int. Cl.$^5$ ................ C07C 209/00; C07C 209/48; C07C 209/62; C07C 209/64
[52] U.S. Cl. .................... 564/469; 544/162; 544/178; 544/185; 544/186; 544/402; 544/404; 546/184; 546/246; 548/569; 548/579; 554/51; 554/56; 554/68; 564/159; 564/488; 564/489; 564/490; 564/491; 564/503; 564/505; 564/508; 564/511; 564/512
[58] Field of Search ........... 564/469, 159, 488, 489, 564/490, 491, 503, 505, 508, 511, 512; 544/162, 178, 185, 186, 402, 404; 546/184, 246; 548/569, 579; 554/51, 56, 68

[56] References Cited

U.S. PATENT DOCUMENTS

| | | | |
|---|---|---|---|
| 4,002,564 | 1/1977 | Carbonel et al. | 210/688 |
| 4,366,321 | 12/1982 | Shuttleworth et al. | 549/68 |
| 5,109,074 | 4/1992 | Eiffler et al. | 525/340 |
| 5,180,833 | 1/1993 | Uneme et al. | 548/202 |

FOREIGN PATENT DOCUMENTS 946622 7/1956 Fed. Rep. of Germany .
2545695 11/1975 Fed. Rep. of Germany .
860922 2/1961 United Kingdom .

Primary Examiner—Richard L. Raymond
Assistant Examiner—Scott C. Rand
Attorney, Agent, or Firm—Burns, Doane, Swecker & Mathis

[57] ABSTRACT

The methylated tertiary amines are selectively prepared by reacting a primary or secondary amine, or a nitrile or aminonitrile, including an aminoalcohol, etheramine, a polyamine or fatty polyamine or amidoamine, or amidopolyamine or dinitrile, with hexamethylenetetramine ("HMTA"), under hydrogen pressure at a temperature no greater than about 160° C. and in the presence of a catalytically effective amount of a hydrogenation catalyst, e.g., nickel deposited onto appropriate support substrate therefor.

19 Claims, No Drawings

HMTA PREPARATION OF METHYLATED TERTIARY AMINES

BACKGROUND OF THE INVENTION

1. Field of the Invention

The present invention relates to the preparation of methylated tertiary amines, and, more especially, to the preparation of methylated tertiary amines by reacting hexamethylenetetramine with certain nitrogen compounds in the presence of hydrogen and a hydrogenation catalyst.

The monomethylated or dimethylated tertiary amines which can be prepared according to the present invention constitute a wide variety of cyclic and acyclic amines having, inter alia, the following general formulae:

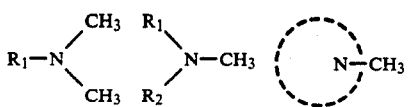

These also comprise the polyamines and mixed amines and polyamines.

2. Description of the Prior Art

The mono- or dimethylated tertiary amines comprise at least three types of compounds that are extensively researched in industry, e.g., quaternary ammonium salts, betaines and amine oxides, which find numerous applications in detergents, cosmetics, as bactericides, antibiotics, as agents for treating textiles, or for making organophilic clays.

Numerous processes are known to this art for preparing methylated tertiary amines, for example the direct methylation of primary or secondary amines by means of various methylation reagents such as methyl chloride or sulfate, or by the formaldehyde/formic acid system (Leuckart-Wallach reaction; see *Merck Index*, 10th Edition, p. ONR-55), by the hydrogenation of dialkylamides (EP-412,359 (Hoechst) or FR-2,633,927 (CECA S.A.)), or by the transformation of nitriles by the formaldehyde/hydrogen system (JP-63/287,752 (Kao Soap)).

These processes, however, present various major disadvantages. For example, those which are based on the Leuckart reaction, which itself is difficult to conduct, produce amines which are contaminated, inter alia, by formaldehyde; others, which entail methylation by methyl chloride, in addition to generating hydrochloric acid, lack selectivity and the resulting products contain quaternary ammonium salts in proportions that are difficult to control. The direct hydrogenation of amides uses a copper chromite catalyst, which is incompatible with the nickel catalyst otherwise employed in plants for preparing amines, and this multiplies the number of processing units required and increases the total cost of production of these plants.

SUMMARY OF THE INVENTION

Accordingly, a major object of the present invention is the provision of an improved process for the preparation of monomethylated and dimethylated tertiary amines that avoids, or conspicuously ameliorates, the above disadvantages and drawbacks to date characterizing the state of this art.

Briefly, the present invention features the preparation of mono- and dimethylated tertiary amines by reacting hexamethylenetetramine ("HMTA") with an amine or a nitrile, in the presence of hydrogen and a catalytically effective amount of a hydrogenation catalyst.

DETAILED DESCRIPTION OF THE PREFERRED EMBODIMENTS OF THE INVENTION

More particularly according to the present invention, hexamethylenetetramine is a well known compound of the formula $C_6H_{12}N_4$, indexed under the "registry number" [RN=100-97-0], and is produced by the condensation of formaldehyde with ammonia. HMTA is a tetracyclic compound, as is indicated by its official name 1,3,5,7-tetraazatricyclo $(3.3.1.1^{3.7})$ decane or, in referring to its spacial configuration, its name is 1,3,5,7-tetraazaadamantane. HMTA is primarily used, not only as an antiseptic, especially in urinary therapy (urotropine), but also as a formaldehyde donor (hardener for phenol/formaldehyde resins), vulcanizing agent for rubbers, and as a corrosion inhibitor for iron. It is also a base capable of providing crystalline salts with mineral or organic acids. HMTA also serves as a tertiary amine in relation to quaternization agents and provides quaternary salts which liberate the corresponding amine upon hydrolysis, which is the reason HMTA functions as an amination agent. (See, for example, K. E. Schulte and M. Goes, *Arch. Pharm.*, 290, 118–30 (1957)).

The general reactions on which the present invention is based can thus be represented by one or the other of the following equations

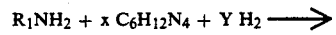
$R_1NH_2 + x\ C_6H_{12}N_4 + Y\ H_2 \longrightarrow$

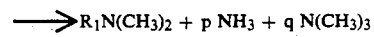
$\longrightarrow R_1N(CH_3)_2 + p\ NH_3 + q\ N(CH_3)_3$

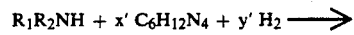
$R_1R_2NH + x'\ C_6H_{12}N_4 + y'\ H_2 \longrightarrow$

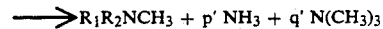
$\longrightarrow R_1R_2NCH_3 + p'\ NH_3 + q'\ N(CH_3)_3$

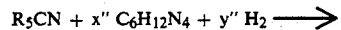
$R_5CN + x''\ C_6H_{12}N_4 + y''\ H_2 \longrightarrow$

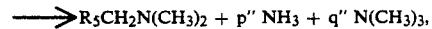
$\longrightarrow R_5CH_2N(CH_3)_2 + p''\ NH_3 + q''\ N(CH_3)_3,$ wherein such formulae the various coefficients $y^i$, $p^i$, and $q^i$ depend on and can be expressed as a function of the respective values of $x^i$. For purposes of simplification, if one considers the methylation of a primary amine, the optimum reaction can be globally represented by the equation:

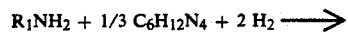
$R_1NH_2 + 1/3\ C_6H_{12}N_4 + 2\ H_2 \longrightarrow$

$\longrightarrow R_1N(CH_3)_2 + 4/3\ NH_3$

In actual practice, the reaction is carried out using an elevated amount of HMTA, especially when it is applied to a precursor having a long fatty chain. The conversion rate of the nitrogenous starting material is governed by the molar ratio x of HMTA to methylatable nitrogen. This ratio is related to the steric hindrance of the nitrogenated site, hence to the structure itself of the precursor starting materials. Hence, it determines the amount of hydrogen consumed y, and the composition of the byproducts of the reaction, NH₃ and trimethylamine, in the gaseous effluent.

Methylation by HMTA is a selective reaction, which connotes that, under the conditions of the invention, only the amine or nitrile functions participate in the reaction. It is thus possible to employ as nitrogenous precursors widely diverse compounds such as aminoalcohols, amidoamines or etheramines. The reaction thus permits the preparation of a wide variety of methylamines from numerous nitrogenous precursors.

The process of the invention permits the preparation of fatty alkyldimethylamines from nitrogenous starting materials comprising a primary amine function, compounds which can be represented by the general formula $R_1NH_2$: true monoamines in which $R_1$ is a hydrocarbon residue R, whether linear or branched, saturated or unsaturated, having from 10 to 22 carbon atoms; aminoalcohols in which $R_1$ is a monovalent residue such as HO—CH₂—CH₂— or HO—CH(CH₃)—CH₂—; etheramines, in which $R_1$ is a group R—O—(CH₂)₃— wherein R is as defined above; etheramines, in which $R_1$ is R—(OCH₂—CH₂)$_p$, R—[OCH(CH₃)—CH₂]$_p$— or R—[OCH₂(CH₃)]$_p$—, in which R is as defined above, and p is a positive number.

The nitrogenous precursors according to the invention can also be simple or complex secondary amines of the general formula $R_1NHR_2$ in which $R_1$ has the same definition as above, $R_2$ may be CH₃ or $R_1$, and $R_1$ and $R_2$ may also comprise a ring member, and, in the case of a cyclic amine, may comprise a second nitrogen heteroatom or oxygen, as the case may be.

The subject methylation by means of HMTA is obviously applicable to polyamines, beginning with the α,ω-diamines, H₂N—(CH₂)$_r$—NH₂ in which r is a integer equal or superior to 2 and which may be very large, although in actual practice one does not exceed values of 14 to 16. In general, the polyamines can be represented by the formula:

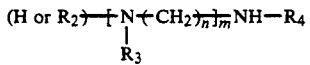

in which $R_1$ is as defined above; $R_2$ is CH₃ or $R_1$; $R_3$ is hydrogen, CH₃: or $R_4$ is H, CH₃, R or $R_1$; n is an integer equal to 2 or 3; and m is a number greater than 1, with the proviso that $R_2$ and $R_3$ may together form a cyclic amine or a nitrogenous ring member and may contain another nitrogen or oxygen heteroatom.

These polyamines particularly comprise diamines, such as alkylpropylene diamines, which are transformed according to the invention into more or less complex mixtures of methylated polyamines such as:

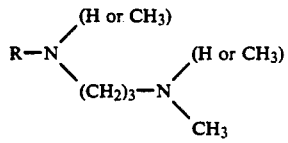

The corresponding derivatives comprising a fatty chain, and more particularly a tallow chain, are of significant value industrially. Indeed, the fatty alkylpropylenediamines having a tallow base are compounds that are widely used in the road building industry as emulsifiers for asphalt. They present the disadvantage of being solid or pasty. On the other hand, the methylated diamines that are prepared according to this invention retain such remarkable emulsifying properties, but have much lower melting points, which greatly facilitates their handling and the dosage metering of same. In addition, they are precursors of quaternary alkylpropylene diammonium chlorides which are likewise useful in the road building industry.

Among the many other polyamines useful as starting materials for the process of the invention are the fatty polyamines which are linear or branched at the nitrogen atom and have one of the following general formulae:

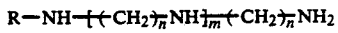

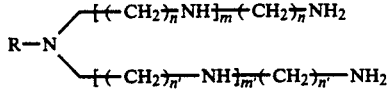

in which R is a hydrocarbon chain having 10 to 22 carbon atoms; n and n' are the integers 2 or 3; and where m and m' are any number ranging from 0 to 3.

These compounds, and notably the polyamines comprising a tallow chain which can be represented by the first of the above formulae, and in which n is 3 and m is an average number ranging from about 2 to 3, are likewise useful in the road building industry as dopes for adhesivity and as emulsifiers for asphalt; methylation according to the invention transforms them into compounds of controlled melting point, which depends on the extent of alkylation.

The fatty amidoamines or amidopolyamines, which are industrial compounds often used in competition with those indicated above, can be represented by the formula:

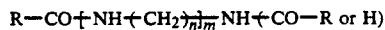

in which R is a hydrocarbon residue as indicated above, n generally is 2 or 3, and m is any number ranging from 1 to 6, as well as their derivatives which are more or less cyclized into imidazolines or tetrahydropyrimidines, and are equally methylatable via the process of the invention.

The process of the invention also features the preparation of methylated amines directly from nitriles, whether from fatty mononitriles, from simple or complex amines such as:

wherein $R_5$ is R as defined above or R—O—(-(-CH₂-)₂—, and also from aminonitriles having the formula:

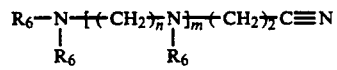

in which the radicals $R_6$ may independently be either H or CH₃ or $R_1$, with the proviso that two radicals $R_6$ depending from the same nitrogen atom may together form, with said nitrogen atom from which they depend, a cyclic amine which may include another oxygen or nitrogen heteroatom; n is an integer having the value of 2 of 3; and m is any integer or any number ranging from 0 to 3. The selectivity of the reaction indicated above permits methylation, simultaneously, of precursor amines and nitriles, without adversely affecting the other functional groups that may be present.

Exemplary of such other starting materials are the dinitriles of the formula:

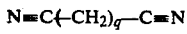

in which q is an integer having a value equal to or greater than 2, but in practice not exceeding 14, and the aminonitrile intermediates of the industrial synthesis of polyamines by cyanoethylation, having one or the other of the following formulae:

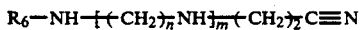

or

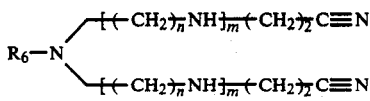

in which $R_6$ is H or $CH_3$ or $R_1$, n is an integer having the value of 2 or 3, and m is any number ranging from 0 to 3.

In general, the preparation of methylated tertiary amines according to the invention by reacting nitrogenous precursors with HMTA is conducted on supported nickel catalysts, under a hydrogen pressure ranging from 3 to 50 bars, and at temperatures not exceeding 160° C.

The process of the invention presents the advantage of avoiding the formation of foams such as those which substantially interfere with the progress of processes based on the Leuckart reaction. The subject reactions produce tertiary amines with only limited byproducts, both qualitatively and quantitatively; it is therefore not necessary to employ repeated washings to eliminate impurities from the final product. It is likely for this reason that the quaternary derivatives (quaternary ammonium salts or betaines) formed from methylalkylamines prepared according to the invention do not exhibit the rose discolorations which adversely affect such products when they are prepared via prior art techniques.

In order to further illustrate the present invention and the advantages thereof, the following specific examples are given, it being understood that same are intended only as illustrative and in nowise limitative.

EXAMPLE 1

Methylation of the monoamine of coconut oil (copra)

Into a two-liter reactor were charged 700 grams of a commercial monoalkylamine (Noram C marketed by CECA S.A., the chain distribution of which being that of the copra acid from which it was produced, namely, primarily chains having 12 to 14 carbon atoms, with an alkalinity equal to 5.20; this product contained about 3.8% by weight of secondary dialkylamines), 363 grams HMTA (molar ratio amine/HMT = 0.70) and 7 grams of a supported nickel catalyst of the type E 230 P (Degussa) containing 63% nickel (i.e., 1% nickel relative to the monoalkylamine).

Under agitation at 1,100/1,500 revolutions per minute, the formed ammonia and trimethylamine were degassed in stages at 130° C. when the consumption of hydrogen was 0, the temperature was then increased to 155° C. and thus the procedure was continued until the total absence of consumption at 155° C. was indicated. The hydrogen pressure was 20 bars. The operation was carried out for 5 to 7 hours.

After separation of the catalyst, the crude amine recovered had the following composition:

| Composition | % by weight |
| --- | --- |
| Monoalkylamines | 0.81 |
| Monomethylmonoalkylamines R—NH—CH$_3$ | 3.7 |
| Dimethylmonoalkylamines R—N—(CH$_3$)$_2$ | 89.1 |
| Dialkylamines R—NH—R | 3.4 |
| Monomethyldialkylamines (R—NCH$_3$—R) | 3.0 |

The heavy dialkyl fractions were separated therefrom by simple distillation; these were present in not insignificant amounts, having been produced from the dialkylamines included in the amine starting material. A mixture having the following composition was thus obtained.

| Composition | % by weight |
| --- | --- |
| Monoalkylamines | 0.9 |
| Monomethylmonoalkylamines R—NH—CH$_3$ | 3.9 |
| Dimethylmonoalkylamines R—N—(CH$_3$)$_2$ | 95.2 |

EXAMPLE 2

Preparation of a dimethylalkylamine from a nitrile

Into a reactor identical to that employed in Example 1 were charged 700 grams of a nitrile based on copra, 1.6% of the same catalyst E 230 P, and 371 g HMTA (molar ratio 0.7). The reaction was carried out under the same conditions as in Example 1.

A product having the following composition was recovered.

| Composition | % by weight |
| --- | --- |
| Monoalkylamines | negligible |
| Monomethylmonoalkylamines R—NH—CH$_3$ | negligible |
| Dimethylmonoalkylamines R—N—(CH$_3$)$_2$ | 76.8 |
| Dialkylamines R—NH—R | 4.5 |
| Monomethyldialkylamines (R—NCH$_3$—R) | 19.7 |

EXAMPLE 3

Preparation of an N-methyldialkylamine of hydrogenated tallow from the corresponding dialkylamine Into a reactor identical to that employed in Example 1 were charged 700 grams of a dialkylamine of hydrogenated tallow (Noram 2SH marketed by CECA S.A.), 1.6% by weight of the same catalyst E 230 P, and 72.3 g HMTA (molar ration amine/HMTA = 1/0.37).

Upon completion of the reaction, a product having the following composition was recovered:

| Composition | % by weight |
|---|---|
| Monoalkylamines | negligible |
| Monomethylmonoalkylamines R—NH—CH$_3$ | negligible |
| Dimethylmonoalkylamines R—N—(CH$_3$)$_2$ | negligible |
| Dialkylamines R—NH—R | 56.0 |
| Monomethyldialkylamines (R—NCH$_3$—R) | 44.0 |

Utilizing a charge of 136 g HMTA, (mole ratio 1/0.70), all other conditions being the same, a product having the following composition was recovered:

| Composition | % by weight |
|---|---|
| Monoalkylamines | negligible |
| Monomethylmonoalkylamines R—NH—CH$_3$ | negligible |
| Dimethylmonoalkylamines R—N—(CH$_3$)$_2$ | negligible |
| Dialkylamines R—NH—R | 28.4 |
| Monomethyldialkylamines (R—NCH$_3$—R) | 71.6 |

The reaction of HMTA with the fatty dialkylamines was particularly interesting in that there resulted no reaction byproduct and that the final product recovered was the methyldialkylamine together with the starting dialkylamine.

EXAMPLE 4

Reaction of diethanolamine with HMTA

Into the apparatus employed in Example 1 were charged 700 g diethanolamine and 346 g HMTA (molar ratio =1/0.35). After reaction under the conditions of Example 1, a product having the following composition was recovered:

| Composition | % by weight |
|---|---|
| Diethanolamine (HOCH$_2$CH$_2$)$_2$NH | 8.1 |
| Methyldiethanolamine (HOCH$_2$CH$_2$)$_2$NCH$_3$ | 91.9 |

The product of this reaction was a simple admixture of the final methyldiethanolamine together with the starting diethanolamine.

Methyldiethanolamine is a useful intermediate for the preparation of aminoesters and their quaternary ammonium derivatives, themselves particularly useful for the formulation of biodegradable textile softeners.

EXAMPLE 5

The procedure of Example 4 is repeated, except that the diethanolamine is replaced by monoethanolamine.

Corresponding admixture of monoethanolamine and dimethylethanolamine is thus recovered.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a methylated tertiary amine, comprising reacting a primary or secondary amine, or a nitrile or aminonitrile, with hexamethylenetetramine (HMTA), under hydrogen pressure and in the presence of a catalytically effective amount of a hydrogenation catalyst.

2. The process as defined by claim 1, carried out at a temperature no greater than 160° C.

3. The process as defined by claim 1, comprising reacting a primary monoamine with said HMTA, such primary amine having the formula R$_1$NH$_2$ wherein R$_1$ is a straight or branched, saturated or unsaturated hydrocarbon R having from 10 to 22 carbon atoms, a radical HO—CH$_2$—CH$_2$— or HO—CH(CH$_3$)—CH$_2$—, a radical R—O(CH$_2$)$_3$—, or a radical R—(OCH$_2$—CH$_2$)$_p$—, R—[OCH(CH$_3$)—CH$_2$]$_p$— or R—[OCH$_2$—CH(CH$_3$)-]$_p$—, and p is a positive number.

4. The process as defined by claim 1, comprising reacting a secondary monoamine with said HMTA, such secondary monoamine having the formula R$_1$NHR$_2$ wherein R$_1$ is a straight or branched, saturated or unsaturated hydrocarbon R having from 10 to 22 carbon atoms, a radical HO—CH$_2$—CH$_2$— or HO—CH(CH$_3$)—CH$_2$—, a radical R—O—(CH$_2$)$_3$—, or a radical R—(OCH$_2$—CH$_2$)$_p$—, R—[OCH(CH$_3$)—CH$_2$]$_p$— or R—[OCH$_2$—CH(CH$_3$)]$_p$—, in which p is a positive number, and R$_2$ is methyl or R$_1$, with the proviso that R$_1$ and R$_2$ may together form, with the nitrogen atom from which they depend, a heterocyclic ring member and said heterocyclic ring member optionally containing an additional nitrogen or oxygen heteroatom.

5. The process as defined by claim 3, said primary monoamine comprising monoethanolamine.

6. The process as defined by claim 4, said secondary monoamine comprising diethanolamine.

7. The process as defined by claim 1, comprising reacting a primary diamine with said HMTA, such primary diamine having the formula H$_2$N—(CH$_2$)$_r$—NH$_2$ wherein r is a number at least equal to 2.

8. The process as defined by claim 7, wherein the formula for said primary diamine, r ranges from 2 to 16.

9. The process as defined by claim 1, comprising reacting a polyamine with said HMTA, such polyamine having the formula:

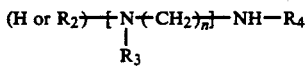

wherein R$_2$ is methyl or R$_1$; R$_3$ is hydrogen, methyl or R$_1$; R$_4$ is hydrogen, methyl, R or R$_1$; R$_1$ is a straight or branched, saturated or unsaturated hydrocarbon R having from 10 to 22 carbon atoms, a radical HO—CH$_2$—CH$_2$— or HO—CH(CH$_3$)—CH$_2$—, a radical R—O—(CH$_2$)$_3$—, or a radical R—(OCH$_2$—CH$_2$)$_p$—, R—[OCH(CH$_3$)—CH$_2$]$_p$ — or R—[OCH$_2$—CH(CH$_3$)-]$_p$—, in which p is a positive number; n is 2 or 3; m is any number greater than 1, with the proviso that R$_2$ and R$_3$ may together form, with the nitrogen atom from which they depend, a heterocyclic ring member and said heterocyclic ring member optionally containing an additional nitrogen or oxygen heteroatom.

10. The process as defined by claim 1, comprising reacting a fatty polyamine with said HMTA, such fatty polyamine having one of the formulae:

or

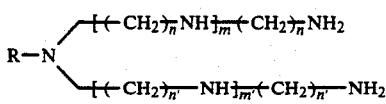

wherein R is a hydrocarbon having from 10 to 22 carbon atoms; n and n' are each 2 or 3; and m and m' are each numbers ranging from 0 to 3.

11. The process as defined by claim 10, said fatty polyamine having the formula:

wherein X is tallow derived.

12. The process as defined by claim 10, said fatty polyamine having the formula:

wherein m is a number ranging from 2 to 3.

13. The process as defined by claim 1, comprising reacting a fatty amidoamine or amidopolyamine with said HMTA, such amidoamine or amidopolyamine having the formula:

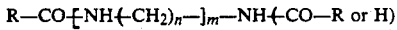

wherein R is a straight or branched, saturated or unsaturated hydrocarbon radical having from 10 to 22 carbon atoms; n is 2 or 3; and m is a number ranging from 1 to 6, or the imidazoline or tetrahydropyrimidine cyclized derivatives thereof.

14. The process as defined by claim 1, comprising reacting a mononitrile with said HMTA, such mononitrile having the formula $R_5-C\equiv N$ wherein $R_5$ is R— or $R-O-CH_2)_2-$, in which R is a straight or branched, saturated or unsaturated hydrocarbon having from 10 to 22 carbon atoms.

15. The process as defined by claim 1, comprising reacting an aminonitrile with said HMTA, such aminonitrile having the formula:

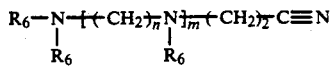

wherein $R_6$ is hydrogen, methyl or $R_1$, with $R_1$ being a straight or branched, saturated or unsaturated hydrocarbon R having from 10 to 22 carbon atoms, a radical $HO-CH_2-CH_2-$ or $HO-CH(CH_3)-CH_2-$, a radical $R-O(CH_2)_3-$, or a radical $R-(OCH_2-CH_2)_p-$, $R-[OCH(CH_3)-CH_2]_p-$ or $R-[OCH_2-CH(CH_3)]_p-$, and in which p is a positive number; with the proviso that two $R_6$ radicals may together form, with the same nitrogen atom from which they depend, a heterocyclic ring member and said heterocyclic ring member optionally containing an additional nitrogen or oxygen heteroatom; n is 2 or 3; and m is a number ranging from 0 to 3.

16. The process as defined by claim 1, comprising reacting a dinitrile with said HMTA, such dinitrile having the formula:

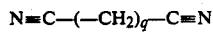

wherein q is a number at least equal to 2.

17. The process as defined by claim 16, wherein the formula for said dinitrile, q ranges from 2 to 14.

18. The process as defined by claim 1, comprising reacting an aminonitrile with said HMTA, such aminonitrile having one of the formulae:

or

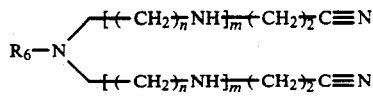

wherein n is 2 or 3; m is a number ranging from 0 to 3; and $R_6$ is hydrogen, methyl or $R_1$, with $R_1$ being a straight or branched, saturated or unsaturated hydrocarbon R having from 10 to 22 carbon atoms, a radical $HO-CH_2-CH_2-$ or $HO-CH(CH_3)-CH_2-$, a radical $R-O(CH_2)_3-$, or a radical $R-(OCH_2-CH_2)_p-$, $R-[OCH(CH_3)-CH_2]_p-$ or $R-[OCH_2-CH(CH_3)]_p-$, and in which p is a positive number.

19. The process as defined by claim 1, said hydrogenation catalyst comprising nickel deposited onto a support substrate therefor.

* * * * *